US010722104B2

(12) United States Patent
Poulsen et al.

(10) Patent No.: US 10,722,104 B2
(45) Date of Patent: Jul. 28, 2020

(54) ENDOSCOPY DEVICE

(71) Applicant: TELEFLEX LIFE SCIENCES PTE. LTD., Singapore (SG)

(72) Inventors: Sylwia Poulsen, Singapore (SG); Teck Poh, Singapore (SG)

(73) Assignee: TELEFLEX LIFE SCIENCES PTE. LTD., Singapore (SG)

( * ) Notice: Subject to any disclaimer, the term of this patent is extended or adjusted under 35 U.S.C. 154(b) by 1009 days.

(21) Appl. No.: 14/911,712

(22) PCT Filed: Aug. 15, 2014

(86) PCT No.: PCT/IB2014/001667
§ 371 (c)(1),
(2) Date: Feb. 11, 2016

(87) PCT Pub. No.: WO2015/022576
PCT Pub. Date: Feb. 19, 2015

(65) Prior Publication Data
US 2016/0192829 A1 Jul. 7, 2016

(30) Foreign Application Priority Data
Aug. 15, 2013 (GB) .................................. 1314631.1

(51) Int. Cl.
*A61B 1/00* (2006.01)
*A61M 16/04* (2006.01)
(Continued)

(52) U.S. Cl.
CPC ...... *A61B 1/00154* (2013.01); *A61B 1/00103* (2013.01); *A61B 1/2733* (2013.01);
(Continued)

(58) Field of Classification Search
CPC ............ A61B 1/00154; A61B 1/00103; A61B 1/2733; A61M 16/0409; A61M 16/0415;
(Continued)

(56) References Cited

U.S. PATENT DOCUMENTS 2,096,831 A 10/1937 Wappler
2,252,874 A 8/1941 Vischer, Jr.
(Continued)

FOREIGN PATENT DOCUMENTS

CN 1166138 11/1997
CN 2579352 Y 10/2003
(Continued)

*Primary Examiner* — Timothy A Stanis
*Assistant Examiner* — Jonathan S Paciorek
(74) *Attorney, Agent, or Firm* — Baker & Hostetler LLP

(57) ABSTRACT

An endoscopy device (1) for facilitating use of an endoscope, comprising at least one airway tube (2) and a mask (3) having a distal end (4), a proximal end (5) and a peripheral formation ξβ) capable of conforming to, and fitting within, the actual and potential space behind the larynx of the patient to form a seal around the circumference of the laryngeal inlet, the peripheral formation (6) establishing separation between a laryngeal; chamber side (3a) and a pharyngeal side (3b), the device further comprising a conduit (8) adapted for passage of an endoscope into the oesophagus of a patient when mask (3) is in place, conduit (8) including a distal end for cooperation with the oesophageal sphincter, the conduit having a laryngeal side (8d), a pharyngeal side (8c), a right side (8e) and a left side (8f), and an outlet wherein at the outlet the width between the left side and the right side is smaller than the width of the conduit.

6 Claims, 3 Drawing Sheets

(51) Int. Cl.
*A61B 1/273* (2006.01)
*A61M 16/08* (2006.01)

(52) U.S. Cl.
CPC .... *A61M 16/0409* (2014.02); *A61M 16/0415* (2014.02); *A61M 16/0447* (2014.02); *A61M 16/0486* (2014.02); *A61M 16/0497* (2013.01); *A61M 16/0816* (2013.01)

(58) Field of Classification Search
CPC .......... A61M 16/0447; A61M 16/0486; A61M 16/0497; A61M 16/0816
See application file for complete search history.

(56) References Cited

U.S. PATENT DOCUMENTS

| | | | |
|---|---|---|---|
| 3,124,959 | A | 3/1964 | Pall et al. |
| 4,096,759 | A | 6/1978 | Desor |
| 4,256,099 | A | 3/1981 | Dryden |
| 4,445,366 | A | 5/1984 | Gray |
| 5,237,988 | A | 8/1993 | Mcneese |
| 5,241,956 | A | 9/1993 | Brain |
| 5,339,808 | A * | 8/1994 | Don Michael ........ A61M 16/04 128/200.26 |
| 5,620,408 | A * | 4/1997 | Vennes .............. A61B 1/00154 128/200.26 |
| 5,632,271 | A * | 5/1997 | Brain .................... A61M 16/04 128/207.15 |
| 5,653,229 | A | 8/1997 | Greenberg |
| 5,935,084 | A | 8/1999 | Southworth |
| 6,079,409 | A | 6/2000 | Brain |
| 6,257,238 | B1 * | 7/2001 | Meah ................ A61B 1/00154 128/200.26 |
| 6,578,576 | B1 | 6/2003 | Taormina |
| 7,762,261 | B1 | 7/2010 | Fortuna |
| 7,895,497 | B2 | 2/2011 | Pisek et al. |
| 2002/0026178 | A1 | 2/2002 | Ouchi |
| 2004/0089307 | A1 | 5/2004 | Brain |
| 2005/0066975 | A1 | 3/2005 | Brain |
| 2005/0081861 | A1 | 4/2005 | Nasir |
| 2006/0118120 | A1 | 6/2006 | Russo |
| 2006/0180156 | A1 | 8/2006 | Baska |
| 2006/0201516 | A1 | 9/2006 | Petersen et al. |
| 2008/0041392 | A1 | 2/2008 | Cook |
| 2008/0276936 | A1 | 11/2008 | Cook |
| 2010/0030027 | A1 * | 2/2010 | Bastid ............... A61M 16/0488 600/120 |
| 2011/0220117 | A1 * | 9/2011 | Dubach ................ A61M 16/04 128/207.14 |
| 2011/0226256 | A1 | 9/2011 | Dubach |
| 2011/0245805 | A1 | 10/2011 | Swinehart et al. |
| 2012/0283513 | A1 * | 11/2012 | Leeflang ........... A61B 1/00071 600/114 |

FOREIGN PATENT DOCUMENTS

| | | |
|---|---|---|
| CN | 1863568 | 11/2006 |
| CN | 2882657 Y | 3/2007 |
| CN | 101057994 | 10/2007 |
| CN | 100531818 | 8/2009 |
| CN | 201516220 U | 6/2010 |
| CN | 201684261 U | 12/2010 |
| CN | 101991898 | 3/2011 |
| CN | 103221087 | 7/2013 |
| DE | 2945662 | 5/1981 |
| EP | 0 389 272 | 9/1990 |
| EP | 1 800 706 | 6/2007 |
| GB | 2454199 | 5/2009 |
| GB | 2436294 | 12/2009 |
| JP | H08-547 | 1/1996 |
| JP | H09-505211 | 5/1997 |
| JP | H10-179745 | 7/1998 |
| JP | 2003-511108 | 3/2003 |
| JP | 2006-522623 | 10/2006 |
| JP | 2008-526393 | 7/2008 |
| TW | 200706196 | 2/2007 |
| WO | WO 00/20062 | 4/2000 |
| WO | WO 06/037626 | 4/2006 |
| WO | WO 06/125986 | 11/2006 |
| WO | WO 07/131267 | 11/2007 |
| WO | WO 09/156949 | 12/2009 |
| WO | WO 10/060224 | 6/2010 |
| WO | WO 10/100419 | 9/2010 |
| WO | WO 13/066195 | 5/2013 |
| WO | WO 2013/079902 | 6/2013 |

* cited by examiner

ENDOSCOPY DEVICE

The present invention relates to an endoscopy device, and more particularly to an endoscopy device that also provides an airway.

Certain surgical and diagnostic endoscopy procedures require the insertion of instruments or viewing devices into the upper gastrointestinal tract of a patient. For example, in endoscopy an endoscope is passed directly through the mouth of the patient, into the oesophagus and down to the stomach and duodenum. The endoscope includes at its tip a light and a visualisation device such as a camera and can include a working channel down which the operator can pass other instruments. In an endoscopy the patient is usually given some form of local anesthetic, and in some cases also a sedative. A mouth guard is placed between the patient's teeth and the endoscope is passed through it, at which point the patient is required to swallow the leading or distal end of the endoscope. Once the patient has swallowed the distal end, the operator must then push the endoscope by manual force down through the oesophagus into the stomach and duodenum.

A number of problems can be experienced with procedures such as endoscopy that require insertion of instruments or viewing devices blind and under manual force into a patient's oesophagus. Firstly, the use of local anaesthetics and sedatives is undesirable in some patients and may cause cardio respiratory complications, including small variations in a patient's vital signs to arrhythmias, respiratory arrest, myocardial infarction, shock and possibly even death (page 7, Complications of Upper Gastrointestinal Endoscopy, Riley and Alderson, BSG Guidelines in Gastroenterology, November 2006). In addition, upper gastrointestinal endoscopy may cause problems such as infection, perforation or in some cases, bleeding. Specifically, perforation may take place in the pharynx or oesophagus of a patient, often at sites of pathology or as a result of blind insertion of an endoscope (pages 7 and 8, Complications of Upper Gastrointestinal Endoscopy, Riley and Alderson, BSG Guidelines in Gastroenterology, November 2006). Furthermore, it is known that therapeutic upper gastrointestinal endoscopy often takes a longer amount of time than diagnostic endoscopy. In addition, in many cases the use of such a technique may be more uncomfortable for the patient concerned and may require a greater level of intravenous sedation, which combined with intravenous analgesia, may cause cardio respiratory complications (page 8, Complications of Upper Gastrointestinal Endoscopy, Riley and Alderson, BSG Guidelines in Gastroenterology, November 2006).

In addition, following upper gastrointestinal endoscopy, patients may experience some minor discomfort to the throat and abdomen. Although these complaints are generally considered to be minor, one prospective study has found that approximately 2% of patients went on to seek medical advice, with some patients being hospitalised (page 7, Complications of Upper Gastrointestinal Endoscopy, Riley and Alderson, BSG Guidelines in Gastroenterology, November 2006).

At present, an endoscope is usually inserted into the oesophagus of a patient Oil its own, i.e. in the absence of a guide device. This typically Causes problems during general anaesthesia as it may interfere with and obstruct the breathing of the patient, due to the fact that little or no air supply is provided. Therefore, in such situations, it is important to carry out the investigative procedure quickly, minimising the amount of time in which the endoscope is inserted. This may result in less information being obtained during the investigative procedure, may be dangerous to the patient and may result in increased costs being incurred.

It is known to use a guide tube to provide a path for travel of an endoscope into a body cavity. EP 2368481 and EP 2368483 relate to a guide device for guiding the entry of an endoscope into a body cavity of a patient.

Artificial airway devices such as the laryngeal mask airway device are well known devices useful for establishing airways in unconscious patients. In its most basic form a laryngeal mask airway device consists of an airway tube and a mask carried at one end of the airway tube, the mask having a peripheral formation often known as a "cuff" which is capable of conforming to and of fitting within, the actual and potential space behind the larynx of the patient so as to form a seal around the laryngeal inlet. The cuff can be inflatable, and in most variants it surrounds a hollow interior space or lumen of the mask, the at least one airway tube opening into the lumen. U.S. Pat. No. 4,509,514 is one of the many publications that describe laryngeal mask airway devices such as this. It is relatively easy to insert a laryngeal mask airway device into a patient and thereby establish an airway. Also, the laryngeal mask airway device is a "forgiving" device in that even if it is inserted improperly, it still tends to establish an airway. Accordingly, the laryngeal mask airway device is often thought of as a "life saving" device. Also, the laryngeal mask airway device may be inserted with only relatively minor manipulation of the patient's head, neck and jaw. Further, the laryngeal mask airway device provides ventilation of the patient's lungs without requiring contact with the sensitive inner lining of the trachea and the size of the airway established is typically significantly larger than the size of the airway established with an endotracheal tube. Also, the laryngeal mask airway device does not interfere with coughing to the same extent as endotracheal tubes. Largely due to these advantages, the laryngeal mask airway device has enjoyed increasing popularity in recent years.

Applicant's own WO 2013/079902 A1, incorporated herein by reference, describes an endoscopy device for facilitating the use of an endoscope that combines features of both a guide and an airway into a design that successfully reconciles the opposing design requirements of each type of device. It is an object of the present invention to provide a yet further improved device.

According to a first aspect of the invention there is provided an endoscopy device for facilitating the use of an endoscope, comprising at least one airway tube and a mask carried at one end of the at least one airway tube, the mask having a distal end and a proximal end and a peripheral formation capable of conforming to, and of fitting within, the actual and potential space behind die larynx of the patient so as to form a seal around the circumference of the laryngeal inlet, the peripheral formation surrounding a hollow interior space or lumen of the mask and the at least one airway tube opening into the lumen of the mask, the peripheral formation establishing separation between a laryngeal chamber side and a pharyngeal side, the device further comprising a conduit adapted for passage of an endoscope into the oesophagus of a patient when the mask is in place, the conduit including a distal end for cooperation with the oesophageal sphincter of the patient, the conduit having a laryngeal side, a pharyngeal side, and with respect thereto, a right side and a left side, and an outlet wherein at the outlet the width between the left side and the right side is smaller than the width of the conduit.

The provision of an endoscopy device in accordance with the present invention has the combined benefits of establishing an airway within a patient and protecting the airway from regurgitation or vomiting that might be caused by endoscopy by providing a close cooperation between the oesophageal sphincter of the patient and the distal end of the conduit. Thus, the device of the present invention advantageously assists in the safe and accurate insertion of an endoscope within the oesophagus of a patient, whilst at the same time establishing an airway within the patient.

It is preferred that the endoscopy device is configured such that at the outlet, the pharyngeal side is terminated proximally of the laryngeal side.

It is further preferred that the endoscopy device is configured such that at the outlet, the width of the conduit wall is reduced. Preferably, the width reduction is at the left and the right side of the outlet.

It is preferred that the distal end of the conduit is provided at an angle of about 30 degrees, relative to the longitudinal axis of the conduit.

According to a second aspect of the invention there is provided an endoscopy device for facilitating the use of an endoscope, comprising at least one airway tube having a proximal end and a distal end and a mask carried at the distal end of the at least one airway tube, the mask having a distal end and a proximal end and a peripheral formation capable of conforming to, and of fitting within, the actual and potential space behind the larynx of the patient so as to form a seal around the circumference of the laryngeal inlet, the peripheral formation surrounding a hollow interior space or lumen of the mask and the at least one airway tube opening into the lumen of the mask, the peripheral formation establishing separation between a laryngeal chamber region and a pharyngeal region, the device further comprising a conduit adapted for passage of an endoscope into the oesophagus of a patient when the mask is in place, characterised in that the airway tube comprises a connector at its proximal end, the connector including one or more strap mount comprising a mount bar around which a strap call be removably fixed for securing the device to a patient.

It is preferred that the device further includes a bite block and that the connector is adapted to connect directly to the bite block such that in combination the connector and bite block provide a stable and relatively rigid attachment point for the strap mount.

It is preferred that the connector and bite block are connectable by a push-fit, and in particular that the bite block and connector include correspondingly shaped and mutually co operable male and female parts.

Preferably, the conduit has a large bore diameter. Typically, the conduit has a diameter of between about 5 and 25 mm, more typically between about 10 and 20 mm and most typically about 15 mm, depending on the size of the endoscopy device. Advantageously, the diameter of the conduit allows the passage of an endoscope through the conduit. Thus, the conduit forms an "operating channel" through which a surgeon can view the upper gastrointestinal tract of a patient. In addition, the diameter of the conduit may be varied depending on the anatomy of a patient. Preferably, the radial wall thickness of the conduit is between about 1 to 2 mm.

It is preferred that the endoscopy device includes two strap mounts. Preferably, the or each mount bar is disposed between two arms which extend out from the connector in a direction generally normal to the longitudinal axis of the proximal end of the conduit and airway tube, such that a mount bar is disposed on either side of the proximal end of the device. Preferably, the arms are curved and extend distally, to conform to the anatomy of a patient's head.

It is preferred that the conduit includes an internal sleeve at its proximal end. Preferably, the sleeve is integrally formed with the connector.

Typically, the endoscopy device in accordance with the present invention is inserted into the upper oesophageal sphincter of a patient. Due to the narrow dimensions of this region of the anatomy, careful insertion of the device is required. Typically, the endoscopy device in accordance with the present invention is inserted into the upper oesophageal sphincter by means of the tip of the cuff, which provides guided insertion of the device. Furthermore, the distal flexibility of the tip of the device may assist in tracking the posterior curvature of the throat of a patient upon insertion of the device and reduces trauma to the throat of the patient.

The use of an endoscopy device in accordance with the present invention in combination with an endoscope is safer than use of the endoscope alone and advantageously allows the endoscope to be inserted within the oesophagus of a patient for a longer period of time.

Typically, the peripheral formation may be inflatable. Preferably, the peripheral formation is an inflatable cuff. The cuff is typically capable of conforming to and fitting within the actual and potential space behind the larynx of the patient so as to form a seal around the laryngeal inlet. Typically, the cuff extends from a proximal end to a distal end.

According to a third aspect there is provided a method of inserting an instrument or viewing device into the upper gastrointestinal tract of a patient comprising use of an endoscopy device according to the first or second aspect. Preferably, the device may be adapted for single use.

The invention will further be described by way of example and with reference to the following drawings, in which, FIG. 1 is a perspective view of a device according to the present invention from the laryngeal side;

Figure 1:
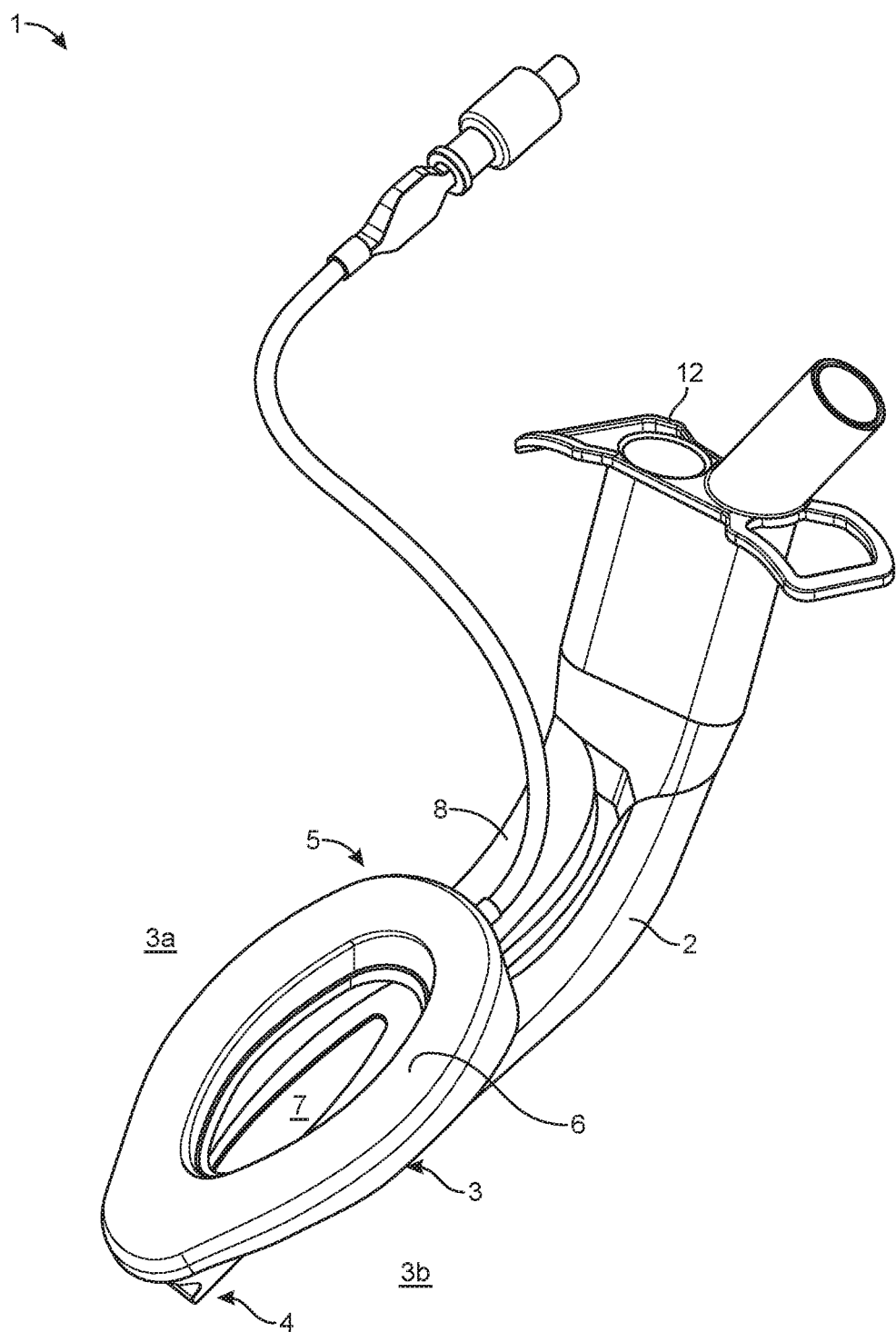

Referring now to the drawings, there is illustrated a device 1 for facilitating the use of a gastroscope, comprising at least One airway tube 2 and a mask 3 carried at one end of the at least one airway tube, the mask 3 having a distal end 4 and a proximal end 5 and a peripheral formation 6 capable of conforming to, and of fitting within, the actual and potential space behind the larynx of the patient so as to form a seal around the circumference of the laryngeal inlet, the peripheral formation 6 surrounding a hollow interior space or lumen 7 of the mask 3 and the at least one airway tube 2 opening into the lumen 7 of the mask, the peripheral formation 6 establishing separation between a laryngeal chamber side 3a and a pharyngeal side 3b the device further comprising a conduit 8 adapted for passage of a gastroscope into the oesophagus of a patient when the mask 3 is in place, the conduit 8 including a distal end for cooperation with the oesophageal sphincter of the patient, the conduit having a laryngeal side 8d, a pharyngeal side 8c, and with respect thereto, a right side 8e and a left side 8f, and an outlet wherein at the outlet the width between the left side and the right side is smaller than the width of the conduit.

In terms of the overall appearance, the device 1 in accordance with the present invention is somewhat similar to prior art laryngeal mask airway devices, in that it consists of the basic parts which makeup most, if not all, such devices, i.e. an airway tube 2 and a mask portion 3. With reference to the Figures, the device 1 has a proximal end 1a (the end nearest user when the device is in use), a distal end 1b (the end farthest from the user when the device is in use), a dorsal or pharyngeal side, a ventral or laryngeal side, and right and left sides.

Figure 5:
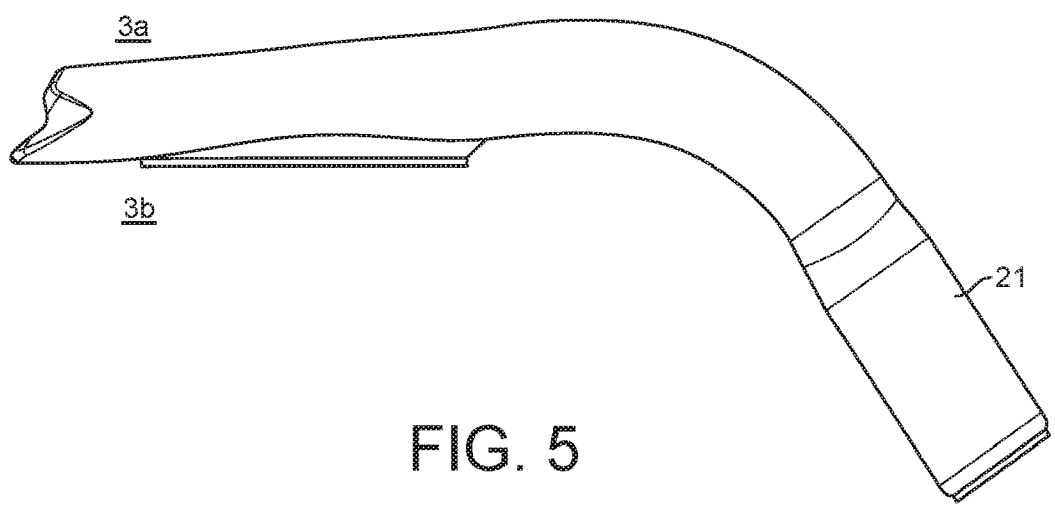
FIG. 5 is a side View of the device in accordance with the present invention.

The airway tube 2, extends from a proximal end 2a to a distal end 2b, and the distal end 2b opens into the interior of the hollow mask portion 3. The airway tube 2 may be resiliently deformable or relatively rigid, to enable it to assist in insertion of the device 1 into a patient, acting as a handle and a guide. The airway tube 2 may be made of any material that is currently used for such purposes as will be apparent to one of skill in the art, for example, silicone rubber or plastics materials. It may be straight and flexible or moulded into an appropriately anatomically-curved shape. As shown in FIG. 5, an angle of about 120° is suitable and has been found to minimise any distortion of the conduit 8 when the device 1 is in position and allow a maximised conduit internal diameter.

Referring to FIG. 1, the mask portion 3 includes a body part often referred to as a backplate 9 and a peripheral formation which may take the form of an inflatable cuff 6, the inflatable cuff 6 extending from a proximal end 6a to a distal end 6b. The inflatable cuff 6 may be provided with to inflation line 14. The inflatable cuff 6 is advantageously capable of conforming to and fitting within the space behind the larynx to form a seal around the circumference of the laryngeal inlet without the device 1 penetrating into the interior of the larynx. Different sizes of mask are needed for different sizes of patient.

The cuff 6 may comprise silicone or blow moulded PVC and may take the form of a generally elliptical inflatable ring. The cuff 6 is typically integrally formed in one piece.

It is preferred that the backplate 9 comprises a dorsal or pharyngeal side and a ventral or laryngeal side. It is preferred that the dorsal surface of the airway tube 2 corresponds in curvature to the curvature across the width of the backplate 9. The backplate 9 is typically formed by moulding from a Shore 50A Vythene PVC+PU. This material is typically substantially softer and more deformable than the material of airway tube 2. The backplate 9 typically comprises a generally oval moulding when viewed from the dorsal or ventral directions.

In contrast to prior art laryngeal mask airway devices, the device 1 according to the invention includes a conduit 8, which conduit 8 is provided to facilitate insertion of a gastroscope, such as a fibrescope or an endoscope, into the oesophagus of a patient when the mask 3 is in place.

The conduit 8 preferably has a relatively large bore diameter. Typically, the conduit has a diameter of between 5 and 25 mm, more typically between 10 and 20 mm and most typically about 15 mm. Such a diameter may be provided to allow the passage of a gastroscope such as an endoscope or fibrescope through the conduit 3. However, the diameter of the conduit 8 may be varied depending on the anatomy of a patient.

Figure 2:
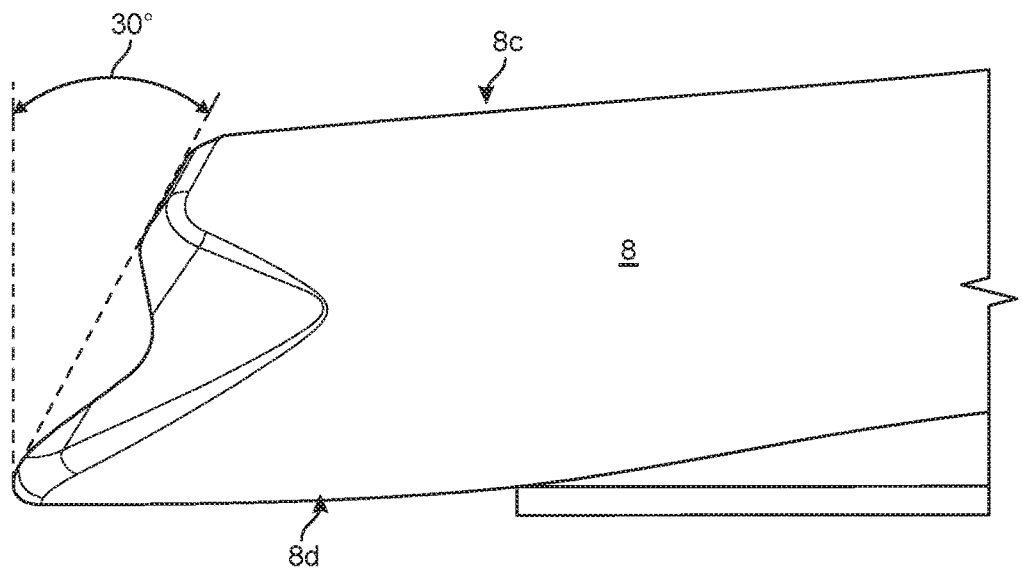
FIG. 2 is a part view of the left side of the device of FIG. 1.

The conduit 8 extends longitudinally along the dorsal surface of the mask portion 3 of the device and contacts the distal end 6b of the cuff 6. Preferably, the conduit 8 is moulded integrally with the backplate 9. The distal end 8b of the conduit 8 extends beyond the distal extent of the backplate 9, traverses the distal end of the cuff 6 and terminates co-terminus with the distal end 6b of the cuff 6 (FIG. 1). Referring now to FIG. 2, it can be seen that the distal end 8b of the conduit 8 is not cut square to, or in other words perpendicular to, its longitudinal axis, but is actually provided at an angle α to the longitudinal axis. Preferably, the angle α is about 30 degrees to the longitudinal axis of the conduit 8. The effect of this is that the pharyngeal side 8c terminates proximally of the laryngeal side 8d and this assists in insertion and sealing of the device 1 within the oesophagus of a patient. Preferably, the distal end 8b of the conduit 8 does not extend significantly beyond the distal end of the cuff 6 (i.e. at the tip of the cuff), such that it does not interfere with the guiding means provided by the tip of the cuff 6 during insertion of the device 1.

Figure 3:
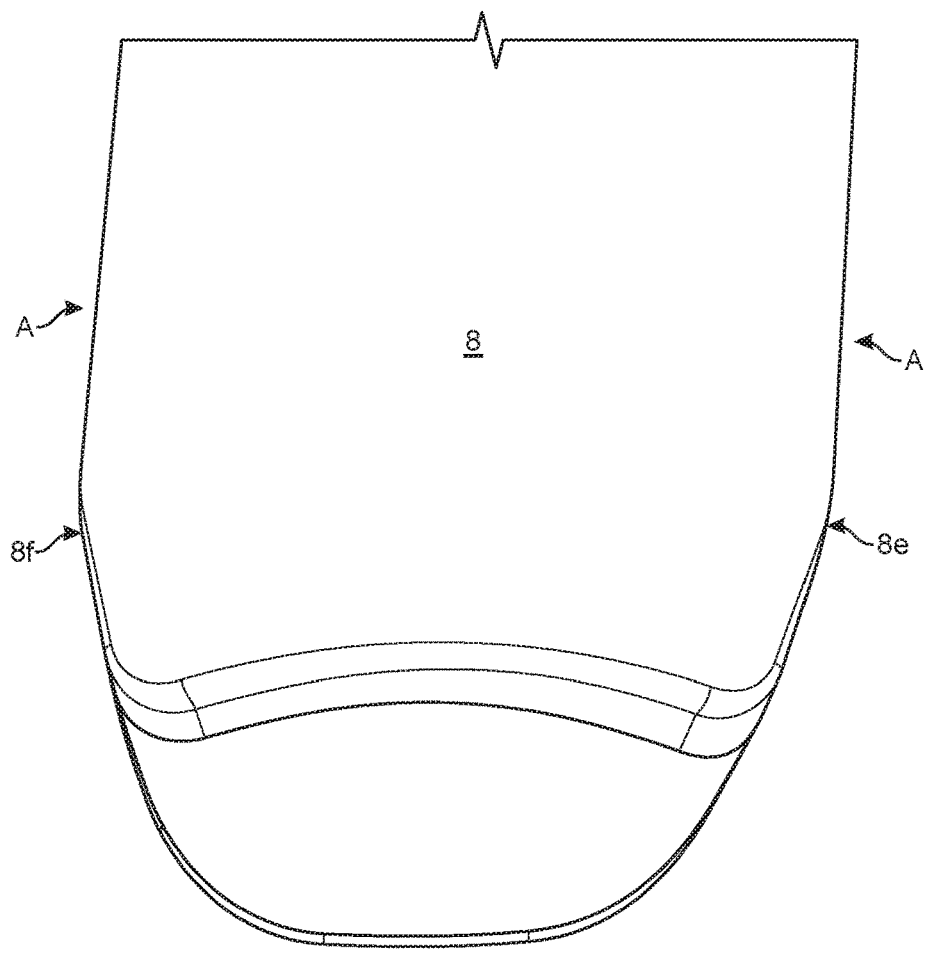
FIG. 3 is an end view of the part of the device of FIG. 1.

Referring particularly to FIGS. 2,3 and 5 it can be seen that the distal end 8b of the conduit 8 is further adapted to aid atraumatic insertion into the upper oesophageal sphincter and also to engage effectively with the anatomy of the patient at that point when inserted. From FIGS. 2 and 3 it can be seen that the conduit 8 has a dorsal or pharyngeal side 8c, a ventral or laryngeal side 8d, and right and left, sides 8e, 8f when viewed from its end as shown in FIG. 3. From FIG. 3 it can be seen that the width of the distal end 8b of the conduit 8, from left to right as viewed, is reduced relative to the width of the majority of the length of the conduit 8, at for example 'A'-'A'. The effect of this is to produce an outlet that more effectively fits into the upper oesophageal sphincter of a patient and also more effectively guides an endoscope into the oesophageal sphincter of the patient. At the same time it can be seen from FIG. 2 that the reduction in width is achieved at least in part by removing material from the outer surface of the conduit 8 wall at points adjacent the outlet on the right and left side, resulting in the provision of parts 108 which are relatively thinner them the rest of the conduit wall. Parts 108 allow the distal end 8b of conduit 8 to be flattened relatively easily in the dorsal to ventral direction which has the effect of making the device easier to insert whilst providing a smooth transition portion at these points and which can be extended to a lesser degree around the entire circumference of the outlet. This ensures that there are no sharp edges to cause trauma to the anatomy on insertion and provides sealing surfaces that seal with the anatomy when the device 1 is in position.

Throughout most of its length, the conduit 8 may conveniently be moulded or extruded from a flexible or elastomeric material such as silicone or other plastic or rubber, preferably of a durometer hardness in the range 60 to 70 Shore. For use in adult humans, the inner diameter (i.d.) of the conduit 8 may be about 15 mm, and the radial wall thickness may be about 1 to 2 mm.

Figure 4:
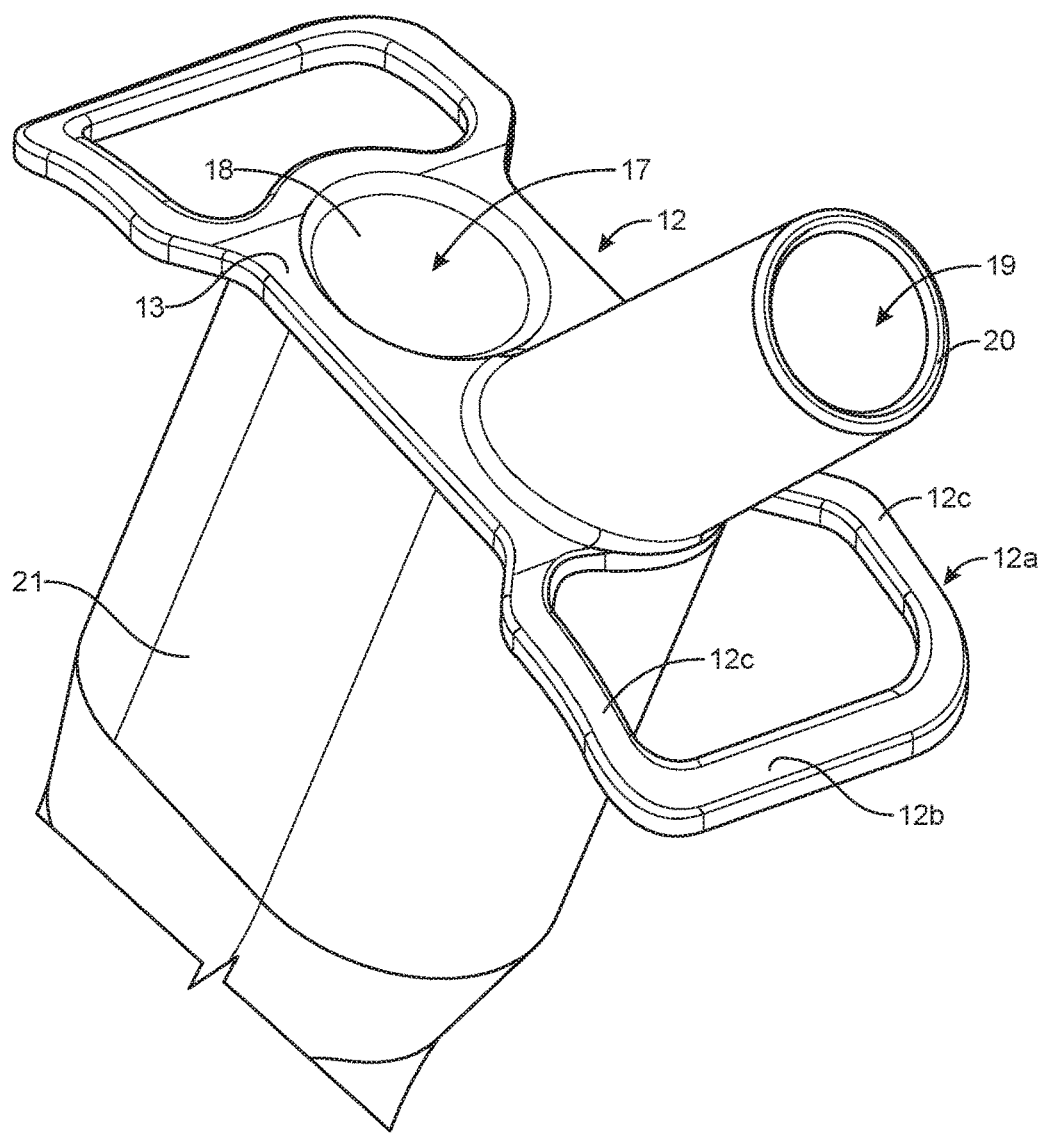
FIG. 4 is an isometric view of a part of a device in accordance with to aspect of the invention.

FIG. 1 shows a device in accordance with one embodiment of the present invention, wherein a connector 12 is provided at the proximal end 2a of the airway tube 2. In this embodiment, the connector 12 allows for connection of the airway tube 2 to a gas supply. The connector 12 is formed from a relatively rigid plastics material (when compared with the airway tube 2), to enable ease of connection of air lines and suction. Referring now to FIGS. 1 and 4 there is illustrated an endoscopy device for facilitating the use of an endoscope, comprising at least one airway tube having a proximal end and a distal end and a mask carried at the distal end of the at least one airway tube, the mask having a distal end and a proximal end and a peripheral formation capable of conforming to, and of fitting within, the actual and potential space behind the larynx of the patient so as to form a seal around the circumference of the laryngeal inlet, the peripheral formation surrounding a hollow interior space or lumen of the mask and the at least One airway tube opening into the lumen of the mask, the peripheral formation establishing separation between a laryngeal chamber region and a pharyngeal region, the device further comprising a conduit adapted for passage of an endoscope info the oesophagus of a patient when the mask is in place, characterised in that the airway tube comprises a connector 12 at its proximal end, the connector including one or more strap mount 12a comprising a mount bar 12b around which a strap (hot shown) can be removably fixed for securing the device to a patient.

From FIG. 4 it can be seen that the illustrated device 1 includes two strap mounts 12a, but it is envisaged that a single strap mount could be provided, depending from a point on either the dorsal or ventral side of the connector 12. In either case, each strap mount 12a includes a mount bar 12b held in position by two arms 12c which extend out from the connector in a direction generally normal to the longitudinal axis of the proximal end of the conduit and airway tube such that a mount bar 12b is positioned on either side of the proximal end of the device, A strap can thus be attached to the mount bars and placed around the patient's head to keep the device 1 in position. In a variation, the arms 12c can be curved in the direction of the mask portion of the device 1 so that each strap mount mimics to some degree the Curvature of the patient's anatomy, which gives a more secure and comfortable fixation. As can be seen from FIG. 4, the connector 12 includes a plate 13 from which arms 12c extending a first through bore 17 with sleeve 18 and a second through bore 19 with sleeve 20. Sleeve 18 fits into the distal end of conduit 8 by an interference fit to assist in keeping the connector in place. Sleeve 20 also passes a short distance into the airway tube bore for the same purpose, but also extends out therefrom for connection of a gas supply. Sleeve 20 is angled away form sleeve 18 so as not to interfere with insertion of an endoscope.

In this embodiment, the distal ends of conduit 8 and airway tube 2 are housed within an integrally formed bite block 21, which forms a relatively rigid structure onto which the connector 12 is fitted. This arrangement ensures that unwanted flexing of the conduit and airway tube is avoided on insertion of an endoscope and provides a stable base for strap mounts 12a.

As shown in FIG. 1, the device 1 also preferably includes an inflation line 14 for selectively inflating and deflating the inflatable cuff 6, which inflation line 14 extends from a distal end 14b that is coupled to the proximal end 6a of cuff 6 to a proximal end 14a that is located outside of the patient when the device 1 is in use. A check valve 16 is typically located within the flexible tube of the inflation line 14.

In use, the device 1 is inserted through a patient's mouth and down through the throat past the epiglottis until the mask 3 comes to rest with the distal end of the cuff 6b in the base of the throat, lying against the upper end of the normally closed oesophagus (which the mask 3 cannot easily enter because of its dimensions). The cuff 6 is then inflated to seal around the inlet to the larynx.

After insertion of the device, a gastroscope such as a fibrescope or ah endoscope may be inserted through the conduit 8. Thus, an airway is established within a patient by means of the airway tube 2 and a gastroscope may simultaneously be inserted through the conduit 8.

Thus, it has been demonstrated that the present invention provides a device that enables the safe and accurate insertion of an endoscope into the oesophagus of a patient, whilst at the same time establishing an airway and protecting the airway from vomiting or regurgitation that may occur upon insertion of an endoscope.

The invention claimed is:

1. An endoscopy device for facilitating the use of an endoscope, comprising at least one airway tube having a proximal end and a distal end and a mask carried at the distal end of the at least one airway tube, the mask having a distal end and a proximal end and a peripheral formation capable of conforming to, and of fitting within, the actual and potential space behind the larynx of the patient so as to form a seal around the circumference of the laryngeal inlet, the peripheral formation surrounding a hollow interior space or lumen of the mask and the at least one airway tube opening into the lumen of the mask, the peripheral formation establishing separation between a laryngeal chamber region and a pharyngeal region, the endoscopy device further comprising a conduit adapted for passage of an endoscope into the oesophagus of a patient when the mask is in place, characterised in that the airway tube comprises a connector at its proximal end, the connector including one or more strap mount comprising a mount bar to which a strap can be removably fixed for securing the endoscopy device to a patient, wherein the conduit includes an internal sleeve disposed within the conduit at its proximal end, wherein the sleeve is integrally formed with the connector and adapted for passage of the endoscope through the sleeve into the conduit.

2. An endoscopy device according to claim 1, including two strap mounts.

3. An endoscopy device according to claim 2, wherein the or each mount bar is disposed between two arms which extend out from the connector in a direction generally normal to the longitudinal axis of the proximal end, of the conduit and airway tube, such that a mount bar is disposed on either side of the proximal end of the endoscopy device.

4. An endoscopy device according to claim 3, wherein the arms are curved and extend distally, to conform to the anatomy of a patient's head.

5. A method of inserting an instrument or viewing device into the upper gastrointestinal tract of a patient comprising the use of the endoscopy device according to any one of claims 1 to 4.

6. The method according to claim 5 wherein the endoscopy device is adapted for single use.

\* \* \* \* \*